United States Patent [19]

Arquint et al.

[11] Patent Number: 5,344,977
[45] Date of Patent: Sep. 6, 1994

[54] PROCESS FOR THE PREPARATION OF 2,3-DIBROMOPROPIONYL CHLORIDE

[75] Inventors: Alfons Arquint; Peter Leupin, both of Basel, Switzerland

[73] Assignee: Ciba-Geigy Corporation, Ardsley, N.Y.

[21] Appl. No.: 8,056

[22] Filed: Jan. 22, 1993

Related U.S. Application Data

[63] Continuation of Ser. No. 699,543, May 14, 1991, abandoned.

[30] Foreign Application Priority Data

May 17, 1990 [CH] Switzerland ............... 1666/90-0

[51] Int. Cl.$^5$ ............... C07C 53/19; C07C 53/42; C07C 53/50
[52] U.S. Cl. ............... 562/864; 562/861; 562/862; 562/863
[58] Field of Search ............... 562/861, 862, 863, 864

[56] References Cited

U.S. PATENT DOCUMENTS

| | | | |
|---|---|---|---|
| 1,805,162 | 5/1931 | Britton | 562/862 |
| 3,364,259 | 1/1968 | Scigliano et al. | 260/544 |
| 4,039,523 | 8/1977 | Hegar | 534/618 |
| 4,065,446 | 12/1977 | Bien et al. | 534/582 |
| 4,528,146 | 7/1985 | Bockmann et al. | 562/86.3 |
| 4,801,694 | 1/1989 | Scheibli et al. | 534/637 |
| 4,855,410 | 8/1989 | Oxenius et al. | 534/591 |
| 4,885,360 | 12/1989 | Scheibli | 534/642 |
| 4,892,870 | 1/1990 | Lee | 514/211 |
| 4,917,705 | 4/1990 | Mausezahl et al. | 534/636 |
| 4,990,599 | 2/1991 | Mausezahl et al. | 534/634 |
| 4,994,562 | 2/1991 | Lehmann | 534/599 |

FOREIGN PATENT DOCUMENTS 0163342  10/1982  Japan ............... 562/862

OTHER PUBLICATIONS

Streitwieser & Heathcock, "Introduction to Organic Chemistry", Macmillan Publishing Co., New York (1976), pp. 444 & 581.
Asinger et al., Journal fur Praktische Chemie, 314, pp. 80–86 (1972).
Pizey, "Synthetic Reagents," vol. 1, pp. 333–335 (1974).
R. S. Davidson et al., J. Soc. Dyers Colour, vol. 104(2), pp. 86–93 (1988).

Primary Examiner—José G. Dees
Assistant Examiner—Barbara S. Frazier
Attorney, Agent, or Firm—Kevin T. Mansfield

[57] ABSTRACT

An improved process for the preparation of 2,3-dibromopropionyl chloride, which comprises brominating acrylic acid, adding iron powder or an iron salt to the resultant melt, chlorinating the dibromopropionic acid obtained, and removing the volatile components. The 2,3-dibromopropionyl chloride is obtained in high yield and purity and is an intermediate for synthesising in particular reactive dyes.

3 Claims, No Drawings

PROCESS FOR THE PREPARATION OF 2,3-DIBROMOPROPIONYL CHLORIDE

This application is a continuation of application Ser. No. 07/699,543, filed May 14, 1991, now abandoned.

The present invention relates to an improved single step process for the preparation of 2,3-dibromopropionyl chloride, which comprises the steps of:
a) brominating acrylic acid,
b) adding iron powder or an iron salt to the resultant melt,
c) chlorinating the dibromopropionic acid obtained to 2,3-dibromopropionyl chloride, and
d) removing the volatile components.

The 2,3-dibromopropionyl chloride obtained by the process of this invention is obtained in high yield (over 97%) and high purity (more than 98%).

2,3-Dibromopropionyl chloride is, as reactive component, an important intermediate for the synthesis of reactive dyes.

The inventive feature consists in adding iron powder or an iron salt to the resultant melt in accordance with step b) above.

Specifically, the reaction is carried out as follows:
a) Acrylic acid ($CH_2=CH-COOH$) is brominated. Bromination is effected by charging a small excess (~1%) of the brominating agent, preferably liquid bromine, to the reactor and adding acrylic acid dropwise in the temperature range from 20° to 70° C.
b) As soon as a melt has formed and all the acrylic acid has been added, iron powder or an iron salt, conveniently in the form of a 40% aqueous solution, is added in the temperature range from 20°–70° C. to this melt. It is advantageous to add 0.01 to 2.0 mol %, preferably 0.1 to 0.3 mol %, most preferably 0.2 mol %, of iron powder or iron salt (based on the acrylic acid). Particularly suitable iron salts are: iron(III) chloride, iron(II) chloride, iron(II) iodide, iron(II) nitrate, iron(III) bromide, iron(II) oxide, iron(III) oxide, iron(II) hydroxide, iron(III) hydroxide and iron(II) sulfate. The preferred iron salt is iron(III) chloride. The addition of the iron powder or iron salt is followed by the step of
c) chlorinating the dibromopropionic acid ($CH_2.Br-CH.Br-COOH$) to 2,3-dibromopropionyl chloride ($CH_2.Br-CH.Br-COCl$) by adding the chlorinating agent, preferably thionyl chloride, over 3 to 10 hours uniformly in the temperature range from ca. 55° to 75° C., preferably at 65° C., with stirring, to the melt (conveniently using an excess of 1–30%, preferably 5–25% and, most preferably, 15–22% of chlorinating agent), to give a reaction mass which contains more than 95% of 2,3-dibromopropionyl chloride, and from which
d) the volatile components, in particular HCl and $SO_2$ and excess thionyl chloride, are removed over the course of 1–2 hours, conveniently by vacuum distillation, for example applying a vacuum of up to 25 mbar.

The invention is illustrated by the following non-limitative Examples.

EXAMPLE 1

The reactor is charged with 224 g of bromine at 15°–20° C. With stirring, 100 g of acrylic acid are added uniformly over 8 hours. Simultaneously the temperature rises and the reaction mixture refluxes. After stirring for 30 minutes at 64°–66° C., a melt of 2,3-dibromopropionic acid is obtained. To this melt are then added 1.1 g of iron(III) chloride solution (40% in water). With stirring, 191 g of thionyl chloride ($\triangleq 15\%$ excess) are added uniformly to the melt at 65° C. over 5 hours. Stirring is continued for ca. 1 hour at 65° C. until the evolution of gas has ceased. The crude reaction mass so obtained has a purity of 93–95% and the volatile components are removed by evacuating at 65° C. to 25 mbar and degassing for ca. 1½ hours, to give 344 g of 2,3-dibromopropionyl chloride (98% of theory, based on acrylic acid) in a purity of 98–99%.

EXAMPLE 2

(Comparison Example)

The reactor is charged with 224 g of bromine at 15°–20° C. With stirring, 100 g of acrylic acid are added uniformly over 8 hours. Simultaneously the temperature rises and the reaction mixture refluxes. After stirring for 30 minutes at 64°–66° C., a melt of 2,3-dibromopropionic acid is obtained. With stirring, 280 g of thionyl chloride ($\triangleq 75\%$ excess) are added to the melt at 65° C. over 4–6 hours. Stirring is continued for 18–22 hours at reflux at increasing temperature to 85°–90° C. until the evolution of gas has ceased. The crude reaction mass so obtained has a purity of 75–80%. The excess thionyl chloride is removed by distillation at 60°–70° C. and 100–200 mbar over ca. 2 hours. To remove the volatile components completely, the reaction mass is evacuated at 65° C. to 25 mbar and degassed for 1–2 hours, giving 341 g of 2,3-dibromopropionyl chloride (95% of theory, based on acrylic acid) in a purity of 94–96%.

| Composition of the final product in HPLC (% by weight) | | |
|---|---|---|
| Designation | Ex. 1 with iron(III) chloride | Ex. 2 without iron(III) chloride |
| 2,3-dibromopropionyl chloride (main component) | 98–99% | 94–96% |
| 2-bromoacryloyl chloride (secondary component) | <0.2% | 2–3% |

What is claimed is:
1. A process for the preparation of 2,3-dibromopropionyl chloride, in one reactor without isolation of intermediate compounds, which consists essentially of the following sequence of steps:
   a) brominating acrylic acid with liquid bromine in the temperature range from 20° to 70° C.,
   b) adding iron powder or an iron salt selected from the group consisting of iron(III) chloride, iron(II) chloride, iron(II) iodide, iron(II) nitrate, iron(III) bromide, iron(II) oxide, iron(III) oxide, iron(II) hydroxide, iron(III) hydroxide and iron(II) sulfate to the resultant melt,
   c) chlorinating the dibromopropionic acid obtained to 2,3-dibromopropionyl chloride by adding 5 to 25% excess thionyl chloride thereto uniformly over a period of 3 to 10 hours in the temperature range from 55° to 75° C., substantially in the absence of a solvent, and
   d) removing the volatile components.
2. A process according to claim 1, wherein the iron salt in step b) is iron(III) chloride.
3. A process according to claim 1, wherein 0.01 to 2.0 mol % of iron powder or an iron salt is added in step b), based on the acrylic acid.

* * * * *